United States Patent [19]

Caisey et al.

[11] Patent Number: 5,713,961
[45] Date of Patent: *Feb. 3, 1998

[54] PROCESS FOR BLEACHING HAIR BY LASER IRRADIATION, AND DEVICE

[75] Inventors: Laurence Caisey, Vitry-sur-Seine; Christian Monnais, Neuilly-sur-Seine; Henri Samain, Bievres; Jean-Michel Sturla, Saint-Cloud, all of France

[73] Assignee: L'Oreal, Paris, France

[*] Notice: The term of this patent shall not extend beyond the expiration date of Pat. No. 5,679,113.

[21] Appl. No.: 433,797

[22] Filed: May 3, 1995

[30] Foreign Application Priority Data

May 4, 1994 [FR] France ................... 94 05469

[51] Int. Cl.⁶ ........................................... D06L 3/04
[52] U.S. Cl. .................. 8/103; 8/102; 8/115.52; 8/127.51; 8/444

[58] Field of Search ................... 8/103, 444, 115.52, 8/102, 127.51

[56] References Cited

U.S. PATENT DOCUMENTS

| 3,281,263 | 10/1966 | Priesing et al. | 8/115.52 |
| 4,792,341 | 12/1988 | Kozikowski et al. | 8/103 |
| 5,246,019 | 9/1993 | Godfrey et al. | 8/409 |
| 5,303,722 | 4/1994 | Godfrey et al. | 132/219 |

FOREIGN PATENT DOCUMENTS 9106279  5/1991  WIPO.

Primary Examiner—Alan D. Diamond
Attorney, Agent, or Firm—Nixon & Vanderhye, P.C.

[57] ABSTRACT

The present invention provides a process for bleaching a lock or portion of lock of hair, at least partially, by irradiation of the lock using a laser beam in the form of pulses, and a device for implementation of same.

11 Claims, 2 Drawing Sheets

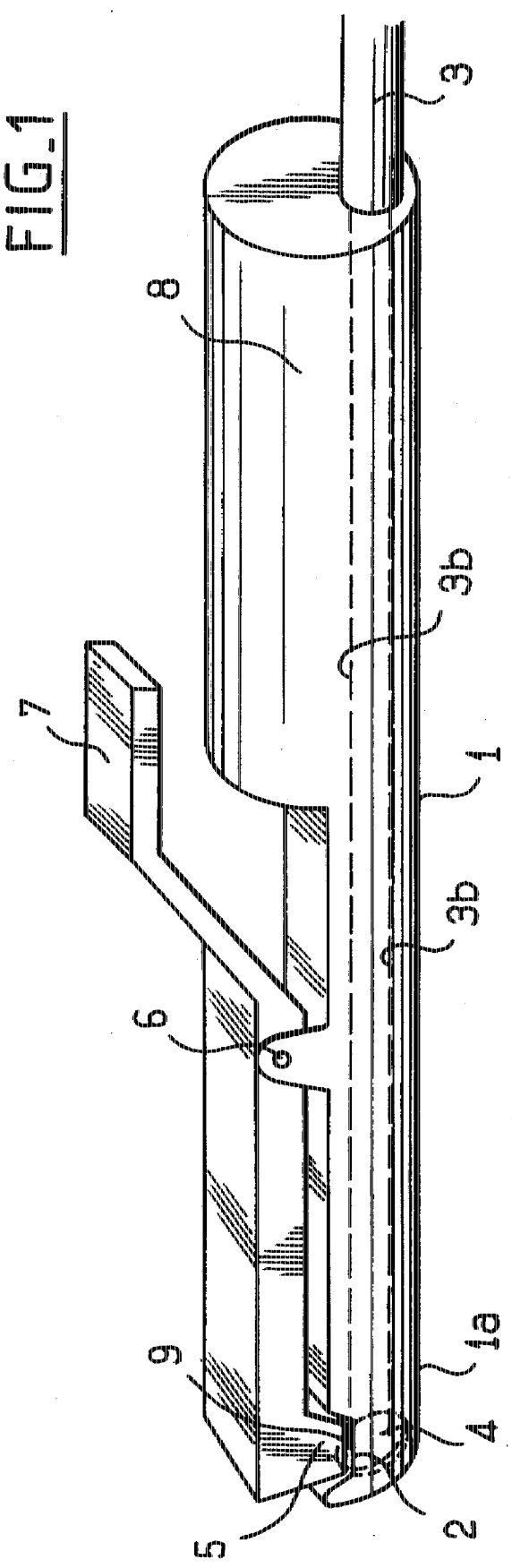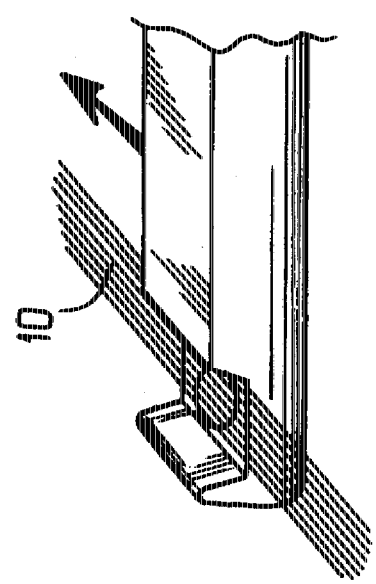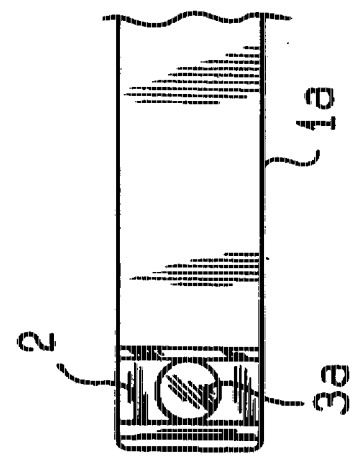

PROCESS FOR BLEACHING HAIR BY LASER IRRADIATION, AND DEVICE

The invention relates to a process for bleaching hair. More precisely, the subject of the invention is a process for bleaching hair by laser irradiation, and a device for implementing this process.

It is known that, in order to bleach or lighten the colour of hair, it is conventional to use a chemical treatment with the aid of an oxidizing agent, such as hydrogen peroxide or persalts, which destroys at least part of the natural and/or artificial colouring substances present in the hair.

The conventional method of chemically bleaching hair requires the use of relatively powerful and/or concentrated oxidizing agents which have the effect of degrading not only the colouring substances but also the keratinous fibre of the hair. The result of this is that hair bleached in this way is fragile and must subsequently be treated with care.

For these reasons, it is impossible for various cosmetic treatments such as for example the permanent-reshaping treatment used for natural hair to be applied to such bleached hair, which treatment consists in applying, to the hair, a reducing agent at relatively high pH values and then an oxidizing agent, and these agents have markedly aggressive effects on the keratinous fibre of the hair. In fact, application of a conventional permanent-reshaping treatment on a bleached head of hair by chemical route causes irreversible degradation and even hair breakages.

Moreover, it is known that a large proportion of people desire to have a so-called "highlighted" head of hair, that is to say a head of hair which has not been totally bleached but in which only certain locks of hair have been bleached. This involves a so-called "highlighting" operation. The case of highlighted heads of hair is particularly tricky since natural hair and highly bleached hair are then encountered on the same head of hair.

The present invention makes it possible to remedy these various drawbacks thanks to a process for bleaching hair by irradiation using a laser beam, under special conditions which make it possible to obtain, on all types of hair, whether coloured naturally or artificially, bleaching of easily controllable intensity, without appreciable degradation of the keratinous fibre, and the treatment may be quite rapid. This process is particularly well suited for obtaining a highlighted head of hair. Furthermore, the hair bleached in this way keeps the mechanical and physico-chemical properties that it had before bleaching. It may, for example, be subjected immediately to a permanent-waving treatment with conventional permanent-waving compositions.

The theoretical possibility of bleaching hair with laser radiation was mentioned in the publication Tech. *News, Laser Focus*, Vol. 19, No. 9, p.26, September 1983. Furthermore, in U.S. Pat. No. 4,792,341, an experimental device has been described which makes it possible to study the destruction of the melanin of the hair using laser radiation. In fact, this U.S. patent describes neither a process nor a device making it possible, in practice, to apply the laser irradiation to the bleaching of hair.

It has now been discovered that it is possible to bleach locks of hair whatever their original (natural or artificial) colour, without degradation of the keratinous fibre, by successively subjecting parts of the locks of hair to be treated to irradiation by a laser beam as long as a laser-radiation power is chosen which is suitable for the type of hair to be bleached.

Studies on isolated hairs of various origins (European, Japanese, Mexican and Scandinavian natural hair) have made it possible to study the luminous power necessary to obtain good bleaching of hair without degradation of the keratinous fibre, with a single laser pulse (one-shot firing). It has been observed that very dark (Japanese or Mexican) hair does not become sufficiently bleached in depth or shatters under the irradiation when the power per unit area is further increased, for a given pulse duration. By using a peak power less than the highest peak power which, in one-shot firing, for the pulse duration used and for the type of hair under study, does not cause shattering of the keratinous fibre, successive shots were subsequently carried out, in sequences, on the same area of the isolated hairs treated. It has been discovered that the isolated hairs, even very dark hairs of the Japanese or Mexican type, could be bleached without damage by lowering the peak power in this way and by carrying out several successive passes on a treated area, thereby making it possible to bleach firstly the surface layers and then the deeper layers, and eventually the hairs may be completely bleached.

Similar studies performed on locks of hair have enabled it to be established that it is possible to bleach hair arranged in locks, as long as a laser-radiation power suitable for the type of hair treated is selected. This power must be sufficient to degrade or destroy the melanin but must not exceed a certain threshold. It has been discovered that the darker the natural colour of hair, the lower this threshold has to be. This therefore leads to the surprising result that the more difficult the hair is to bleach, the more the laser-radiation power has to be moderated.

As will be obviously apparent to those skilled in the art, it is in fact the energy delivered to the particles of melanin, over a sufficiently short time duration, which has to be high enough to degrade or destroy the melanin. In reality, it is therefore the energy density delivered per unit area, in a sufficiently short time, which has to reach a threshold high enough for the hair to be able to be bleached. In the present application, when one speaks of "power" or "peak power", it should be understood that this is a language simplification as it is in fact the energy delivered during each pulse which is important, and it is therefore necessary to take into account the duration of the pulse which must be, however, not greater than approximately one microsecond (approximate duration of the relaxation time of melanin) in the case of the bleaching of natural hair.

It has also been discovered that it is possible similarly to bleach artificially coloured hair as long as the operation is performed, as for undyed hair, by adapting the power of the laser radiation to the natural colour of the hair. It is only after having performed this preliminary step, corresponding to the degradation of melanin, that the bleaching proper, corresponding to the degradation of the artificial dye, may be undertaken. In fact, the degradation of artificial dyes requires higher energies than the degradation of melanin, such that, if it is desired to degrade the said dyes directly, the hair would be destroyed by the shattering of the keratinous fibre, as in the experiments mentioned hereinabove.

Moreover, it is known that certain old people have a "white" head of hair which in fact has an unattractive yellowish tint. The process of the invention makes it possible to convert this yellowish coloration into pure white.

The subject of the invention is therefore a process for bleaching at least one lock or portion of lock of hair, at least partially, by irradiation of the said lock or portion of lock using a laser beam of sufficient power to bleach the hair, characterized in that:

an area of the said portion of lock is treated by irradiation using a laser beam emitted in the form of pulses in order to bleach, at least partially, the hair in the said area, by degradation of the melanin in the hair, if required, by relative movement of the said lock with respect to the said laser beam, one or more other areas are treated in succession, in a similar way, so as to treat the totality of the said portion of lock, the above treatments are possibly repeated until the desired degree of bleaching is obtained for the said lock or portion of lock, the operation is performed with laser radiation of sufficient power to deliver, per pulse, an energy density of 0.1 to 1.2 J/cm$^2$, and the said chosen energy density is not greater than a threshold above which the keratinous fibre of the hair is damaged, the said threshold being lower the darker the natural colour of the hair to be treated.

It is known that a laser is essentially composed of an active medium rendered amplifying by a pumping mechanism delivering energy to the atoms in a selective way, the said active medium being contained in a resonant cavity. The active medium is then capable of emitting a substantially monochromatic, polarized and coherent light beam. Because of this coherence, a laser beam concentrates a markedly greater energy than that of radiation emitted by a conventional light source.

Certain lasers, especially those with a solid-state active medium, are capable of emitting laser radiation in the form of very short pulses (generally between one femtosecond and one microsecond). The concentration of energy into such short time intervals gives the laser pulse a considerable power, called peak power. In the process of the invention, lasers are preferably used which allow production of controlled pulses. For example, it is possible to use ruby lasers or lasers for which the active medium contains ions of rare earths or of actinides, for example a neodymium-type laser. The construction of such lasers is well known. The active ions may be inserted into a crystalline matrix, such as yttrium aluminium garnet (YAG for short), or into an amorphous matrix such as a glass. The pulse repetition frequency is adjusted using a pumping flashlamp. The available energy may be adjusted using conventional systems, especially polarizers.

Preferably, lasers are used which emit in the near ultraviolet, in the visible or in the near infrared, for example at wavelengths of 300 to 1100 nm. For example, it is possible to use a neodymium-YAG laser which emits at 1.06 μm, possibly with a frequency multiplier which makes it possible, for example, to obtain 532 nm wavelength emission (double the frequency) or 355 nm wavelength emission (three times the frequency).

The peak-power/pulse-duration pair (for example the peak power of the laser beam for a given pulse duration) may be easily determined by taking into account the conditions concerning the energy density per pulse, as a function of the natural colour of the hair, even if dyed hair is involved. More precisely, care must be taken not to exceed a maximum energy density per pulse which is of the order of:

0.35 J/cm$^2$ for very dark brown hair (of the Japanese or Mexican type), 0.4 J/cm$^2$ for dark chestnut hair, 0.5 J/cm$^2$ for light chestnut hair, 0.7 J/cm$^2$ for dark blond hair, 1.2 J/cm$^2$ for light blond hair.

The various data supplied hereinabove relating to the energy density were established for a radiation of 532 nm wavelength. When the wavelength used is different, a correction factor $$\frac{\lambda \text{ nm}}{532}$$

should be applied, as is explained in more detail in the experimental part hereinbelow.

Moreover, it is recalled that the various hair colours may be defined objectively using the luminance (L), according to the C.I.E. system of colorimetric coordinates (L,a,b). In the present application, the hair colours mentioned correspond to the luminance ranges mentioned hereinbelow:

| Hair type | L |
|---|---|
| Japanese or Mexican | less than 18 |
| Dark chestnut | 18–20 |
| Light chestnut | 22–24 |
| Dark blond | 28–35 |
| Light blond | 45–52 |

The process described hereinabove, which corresponds to at least partial bleaching by degradation of the melanin in the hair, must be performed, in all cases, even if hair dyed using a colouring agent is treated and, in this latter case, the bleaching process comprises an additional step of irradiation of the hair, similar to the step described hereinabove, but by laser radiation delivering a higher energy density, sufficient to destroy or degrade the colouring agent; this energy density is especially at least equal to 0.8 J/cm$^2$. It is generally less than 2 J/cm$^2$ at 532 nm.

In order to implement the preliminary step of degradation of the melanin, all that is required is to know the natural colour of the dyed hair to be treated and then irradiation conditions are applied which are suitable for the hair having this natural colour, the said conditions having been determined beforehand, once and for all, by simple routine experiments.

The duration of the pulses may range, for example, from 10 picoseconds to 100 nanoseconds.

The process of the invention obviously requires bleaching the head of hair in locks, by successively irradiating areas of the said lock. Generally, the irradiation area may vary within the range 0.1–2 cm$^2$.

The process of the invention is therefore particularly well suited for obtaining highlighted heads of hair. In order to treat the areas to be bleached in succession, by relative movement of a lock with respect to the laser beam, it is possible to move the lock with respect to the apparatus used for the treatment, or vice versa, and/or to vary the direction of the laser beam periodically so as to perform successive scans of the treated area. This periodic variation in the direction of the laser beam may be achieved, for example, using an oscillating mirror.

It has been observed that, when bleaching is performed by laser shots in sequence, the hair tends to heat up locally. In order for this local heating not to be able to damage the hair, it is advisable to limit the pulse repetition frequency and/or to carry out sufficient relative movements of the treated lock of hair with respect to the laser beam so as to prevent cumulative heating, after which it is possible to return to a previously treated area, having had time to cool down sufficiently, in order to complete the treatment, and so on. In practice, it is easy to determine a suitable pulse repetition frequency and/or an appropriate speed of movement of the lock of hair with respect to the laser beam simply by routine experiments, the said suitable frequency and/or the said appropriate speed being those for which heating potentially damaging to the hair is not observed. For example, it is possible to choose a pulse repetition frequency which can range from 5 to 50 Hz, especially from 10 to 20 Hz.

The treated hair may be dry or wet.

In order to be able to bleach the treated lock of hair under good conditions, it is preferable to arrange this lock in the form of a ribbon of hair and it is then possible to bleach the hair in the treated area by irradiating at least one of the faces of the said ribbon. Preferably, the thickness of the ribbon of hair corresponds to the thickness of approximately 3 to 20 superposed hairs.

According to a particular embodiment, the process of the invention is characterized in that:

the operation is performed using a treatment device which includes a receptacle for the lock of hair to be treated, the surface of the said receptacle having an orifice for the exit of the said laser beam, the hair of the said lock, spread out in the form of a ribbon, is applied, over at least part of its length, to the surface of the said receptacle so that an area to be treated is opposite the said orifice, irradiation of the said area is then carried out, and, by relative movements of the said lock with respect to the laser beam, irradiation of the other areas to be treated is carried out in succession.

Devices allowing such an implementation will be described hereinbelow. With these devices, the relative movements of the lock with respect to the laser beam may be achieved by relative movements of the lock with respect to the said receptacle and/or by periodic variations in the direction of the laser beam, as indicated previously.

One of the advantages of the process of bleaching of hair by irradiation with a laser beam is that it is possible to monitor continuously the bleaching produced and to stop the treatment at the chosen degree of bleaching.

As indicated hereinabove, the main advantage of laser irradiation bleaching is that the hair is not degraded and the mechanical and physico-chemical properties that it had before treatment are preserved. Here there is a considerable advantage since it is possible to perform, on the hair bleached in this way, any other cosmetic treatments without taking special precautions.

Another subject of the invention is a device for implementing the hair-bleaching process as defined previously. This device is characterized in that it includes:

a body equipped with a receptacle, the said receptacle being intended to serve as a housing, over at least part of the length of the hair, for a lock of hair to be treated, the lock being spread out in the form of a ribbon;

and means intended to convey a laser beam so as to irradiate at least one area of a lock of hair arranged in the said receptacle.

In particular embodiments, the device of the invention may also have the following characteristics, taken in isolation or, if required, in combination:

the said receptacle includes a wide-bottomed groove, making it possible to spread out the said ribbon on the said bottom;

the said groove may be associated with a disengageable piece of cooperating shape, capable of being inserted into the said groove, leaving, between the said piece and the bottom of the groove, a space forming a housing for the said ribbon; the said piece be disengaged, for example, by actuating a lever which makes it possible to introduce the lock to be treated into the receptacle or to remove it therefrom; the bottom of the said groove and/or one face of the said piece opposite the said bottom may have an orifice for the exit of a laser beam onto the area to be irradiated;

in another embodiment, the said receptacle includes a groove in the form of a narrow slot emerging at the surface of the said body and having a depth sufficient to allow insertion of the said ribbon over the totality of its width; in a way similar to that mentioned hereinabove for the first embodiment, at least one of the faces opposite the said narrow slot may have an orifice for the exit of a laser beam.

Of course, the receptacle must form a light-tight confined space in order to prevent the laser radiation from causing damage to the user or to his clients.

The invention will now be described with reference to the appended drawings in which:

BRIEF DESCRIPTION OF THE DRAWINGS

FIG. 1 is a diagrammatic view of a first embodiment of the device of the invention, which includes, at its end, a receptacle in the form of a wide-bottomed groove and a cooperating piece which can be actuated by a lever;

FIG. 2 is a partial view from above of the end, carrying the receptacle, of the device of FIG. 1;

FIG. 3 illustrates diagrammatically the mode of use of the device of FIG. 1;

FIG. 1 shows that the device includes a partially hollow elongate body (1) whose front end (1a) of smaller cross-section comprises a receptacle having the shape of a flat-bottomed groove (2). A conduit (3) for the laser beam emerges in the bottom of the groove (2) after being sharply reflected by means of the mirror (4), and forms an exit window (3a) at the surface of the wall (2). The dotted lines (3b) show diagrammatically the propagation of the laser beam inside the body (1) or may represent a waveguide.

Figure 4:
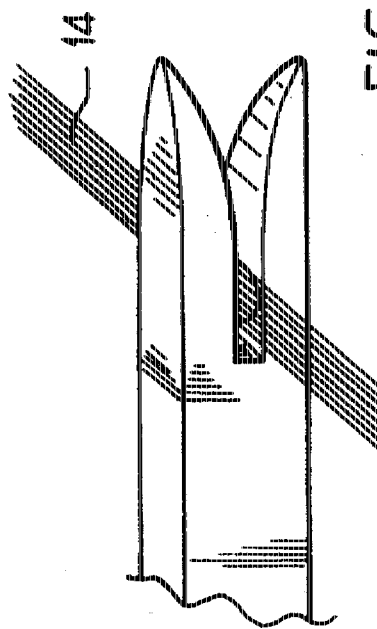
FIG. 4 represents a diagrammatic sectional view of a second embodiment of the device, with a receptacle in the form of a narrow slot.

A cooperating piece (5), which can move about the axis (6), is held engaged in the receptacle by means of return means, such as a tension spring (not depicted), and can be disengaged by actuating the lever (7) with which the piece (5) is equipped at its rear end. The rear part (8) of the body (1) serves as a handle for the apparatus to be gripped by the operator. In order to bleach the hair, the piece (5) is disengaged in order to be able to arrange the lock of hair (10), distributed in the form of a ribbon as indicated in FIG. 3, and then the piece (5) is allowed to re-engage in the groove. The lock therefore lies arranged in the space between the faces (2) and (9), the laser emitter (not represented) is actuated and the device is moved with respect to the lock (or vice versa) in the direction indicated by the arrow in FIG. 3 in order to bleach, in succession, the entire lock or portion of lock to be treated. It is preferable to perform movements which are not too slow, for example of the order of 0.1–5 centimeters per second and to do this in successive passes, to treat the hair to be bleached several times, thereby making it possible to monitor very easily the progress of the bleaching, under good safety conditions. However, it is also possible to use slower speeds of movement or discontinuous movements, for example in combination with a suitable low pulse frequency.

The body of the device my be made of any appropriate material, for example of light metal such as aluminium or of plastic.

Figure 6:
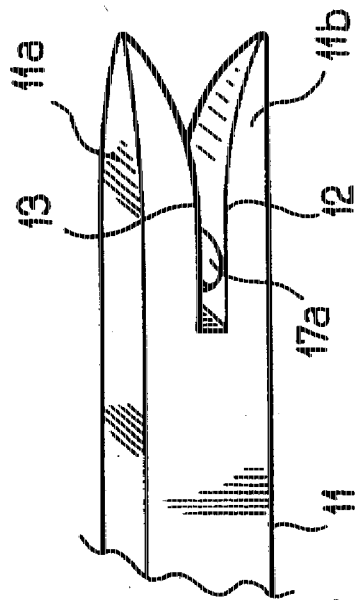
FIG. 6 shows diagrammatically the mode of use of the device of FIG. 4.
Figure 5:
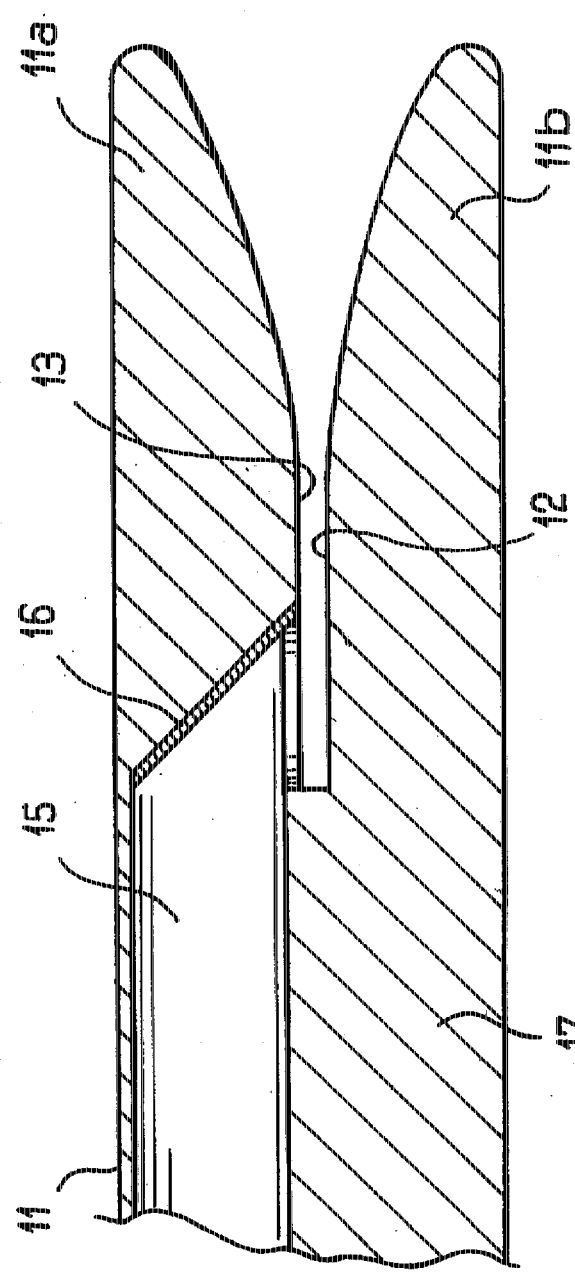
FIG. 5 is a vertical longitudinal sectional view of the device of FIG. 4.

The device represented in FIGS. 4 and 5 comprises an elongate body (11) of which only the front part has been represented, the rear part, not represented, forming the handle. It may be seen that the end of the body (11) splits into two branches (11a) and (11b) separated by a slot whose opposite faces (12) and (13) constitute a housing for a lock of hair (14) arranged as indicated in FIG. 6. As in the first embodiment, a laser channel (15) emerges on the face (13) of the slot, after having been reflected by the mirror (16). This device is used in a similar way to the previous one.

The units for controlling the laser beam and the cooling circuit can be installed on the device or in a separate control unit which may possibly be foot-actuated. It is also possible to provide devices for slaving the laser power as a function of the colour of the lock to be treated, it being possible for this slaving to be carried out automatically after the colour has been read by an appropriate detector.

The following examples illustrate the invention.

EXAMPLE 1

In this example and in the following examples, 0.25 g locks of hair, having a length of 20 cm, are used.

The apparatus used is an apparatus of the type represented in FIG. 1.

The laser radiation source is a Surelite Continuum laser: wavelength 532 nm; shot frequency 1 Hz; beam diameter 5 mm; pulse duration 4 ns.

With this equipment, the ranges of optimal bleaching, depending on the colour of the hair to be treated, have been studied.

The ranges of energy per cm$^2$ for one pulse are those which can be used for bleaching hair effectively.

Below the minimum value, there is no appreciable bleaching. Above the maximum value, the fibre of an individual hair shatters or cracks up (the damage is visible, depending on its size, with a binocular magnifier, a microscope or an electron microscope).

The results are summarized in Table (I) below:

| Hair | energy/cm$^2$ for 1 pulse (in J/cm$^2$) |
|---|---|
| Japanese | 0.2 to 0.35 |
| Dark chestnut | 0.2 to 0.4 |
| Light chestnut | 0.15 to 0.5 |
| Dark blond | 0.15 to 0.7 |
| Light blond | 0.1 to 1.2 |

Moreover, the absorption of luminous energy by melanin varies with the wavelength—it decreases when the wavelength increases, in such a way that the hair withstands, without degradation, a higher incident energy density when the wavelength increases. The experimental study has shown that the maximum energy density which can be withstood by the hair, without the keratinous fibre shattering, for radiation of wavelength λ, is substantially that indicated in the above table, multiplied by a factor $$\frac{\lambda}{532}$$

where λ is expressed in nanometers. This law of variation with wavelength is also valid for the relationship between the incident energy density and the efficiency of the bleaching—the energy density capable of bleaching hair of a given type, for the wavelength λ, is substantially equal to the energy density enabling similar bleaching to be achieved with radiation of 532 nm wavelength, multiplied by the said factor $$\frac{\lambda}{532}$$

For artificially coloured hair, it is necessary to use quite high energy densities, generally at least equal to 0.8 J/cm$^2$ per pulse. If the hair has been coloured without prior bleaching, its natural colour must be taken into account. For example, if the natural colour of the hair was light chestnut, it is necessary firstly to use an energy density not greater than 0.5 J/cm$^2$ (see Table 1 above) in order to bleach the melanin. It is only afterwards that it will be possible to use a higher energy density (1 J/cm$^2$ or more) in order to destroy the artificial dye. If this high energy density were to be applied at the outset, the hair would shatter.

EXAMPLE 2

The procedure is as above, but with a BMI laser having the following characteristics: wavelength 523 nm; shot frequency 10 Hz; beam diameter 3 mm; pulse duration 30 ps.

The peak power per unit area, corresponding to optimum bleaching for dark chestnut hair, is of the order of 9.5 GW/cm$^2$, i.e. an energy per unit area of 0.28 J/cm$^2$.

Furthermore, it has been observed that laser irradiation leaves the alkaline solubility and the cysteic-acid content of bleached hair virtually-unaltered compared to the hair before bleaching, whereas these are greatly increased in the case of bleaching by chemical route.

We claim:

1. A process for bleaching at least one area of a hair lock without appreciable degradation of the keratinous fibers thereof, comprising:

irradiating said at least one area with a laser beam emitted in the form of pulses in order to bleach said at least one area by degradation of melanin contained in said fiber, said irradiating being performed with laser radiation of sufficient power to deliver an energy density per pulse of 0.1 to 1.2 J/cm$^2$, for a wavelength of 532 nm, said energy density being multiplied by a correction factor equal to λ/532 when the radiation has a wavelength of λ nm other than 532 nm; and said energy density being not greater than a threshold above which said degradation of the keratinous fibers occur.

2. The process according to claim 1, further comprising moving said laser beam relative to said hair lock.

3. The process according to claim 1, wherein said energy density per pulse has a maximum of 0.35 J/cm$^2$ for black hair, 0.4 J/cm$^2$ for dark chestnut hair, 0.5 J/cm$^2$ for light chestnut hair, 0.7 J/cm$^2$ for dark blond hair, 1.2 J/cm$^2$ for light blond hair, for a wavelength of 532 nm, said maximum being multiplied by a correction factor equal to λ/532 when the radiation used has a wavelength of λ nm, other than 532 nm.

4. The process according to claim 1, wherein said energy density per pulse, in J/cm$^2$ for a wavelength of 532 nm, is in the range of 0.2–0.35 for dark brown hair, 0.2–0.4 for dark chestnut hair, 0.15–0.5 for light chestnut hair, 0.15–0.7 for dark blond hair, 0.1–1.2 for light blond hair, said ranges being multiplied by a correction factor equal to:

$$\frac{\lambda}{532}$$

when the radiation used has a wavelength λ nm other than 532 nm.

5. The process according to claim 1, wherein said hair lock is arranged, prior to said irradiation, in the form of a ribbon, said irradiating being performed on at least one face of said ribbon.

6. The process according to claim 1, wherein said treatment comprises the use of a device which includes:

(a) a receptacle for a hair lock to be irradiated, said receptacle being provided with a surface having an orifice for the exit of the said laser beam, the hair lock being spread out, in the form of a ribbon, over at least part of its length, onto a surface of the said receptacle so that an area to be irradiated is opposite the orifice, (b) irradiation means to irradiate said area, and (c) movement means for the relative movement of the said hair lock with respect to the laser beam.

7. The process according to claim 6, wherein said relative movement of said hair lock includes relative movement of said hair lock with respect to said receptacle.

8. The process according to claim 6, wherein said relative movement is obtained by periodically varying the direction of the laser beam so as to perform scanning of the area to be irradiated.

9. The process according to claim 7, comprising emitting said pulses at a pulse frequency of from 5 to 50 Hz.

10. A process for bleaching at least one area of a hair lock which is artificially dyed with a coloring agent, comprising:

a) irradiating said at least one area with a laser beam emitted in the form of pulses in order to bleach said at least one area by degradation of melanin contained in said fiber, said irradiating being performed with laser radiation of sufficient power to deliver an energy density per pulse of 0.1 to 1.2 J/cm$^2$, for a wavelength of 532 nm, said energy density being multiplied by a correction factor equal to λ/532 when the radiation has a wavelength of λ nm other than 532 nm, said energy density being not greater than a threshold above which said degradation of the keratinous fibers occurs; and b) subsequently irradiating said at least one area, as in a) above, but with a second energy density, per pulse, which is sufficient to destroy or degrade said coloring agent without degrading said keratinous fibers.

11. The process according to claim 10, wherein said second energy density is at least equal to 0.8 J/cm$^2$ per pulse for 532 nm.

\* \* \* \* \*